(12) United States Patent
Peng

(10) Patent No.: US 9,021,864 B2
(45) Date of Patent: *May 5, 2015

(54) SENSING BIOMOLECULES USING SCANNING PROBE WITH TWIN-NANOPORE TO DETECT A CHANGE IN THE MAGNITUDE OF THE CURRENT THROUGH THE SECOND NANOPORE

(75) Inventor: Hongbo Peng, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 13/590,251

(22) Filed: Aug. 21, 2012

(65) Prior Publication Data
US 2014/0053632 A1    Feb. 27, 2014

(51) Int. Cl.
*G01M 3/02* (2006.01)
*G01N 3/12* (2006.01)

(52) U.S. Cl.
CPC ........................................ *G01N 3/12* (2013.01)

(58) Field of Classification Search
CPC .............. G01N 27/00; G01N 27/4145; G01N 33/48721; G01N 15/12; C12Q 1/68; C12Q 1/6869; B81B 1/00; B82Y 5/00
USPC .......................................... 324/444; 204/452
See application file for complete search history.

(56) References Cited

U.S. PATENT DOCUMENTS

| | | | |
|---|---|---|---|
| 3,890,569 A * | 6/1975 | Hogg | 324/71.1 |
| 5,419,826 A | 5/1995 | Zirino | |
| 5,738,774 A | 4/1998 | Harrison et al. | |
| 7,005,264 B2 | 2/2006 | Su et al. | |
| 7,329,111 B2 | 2/2008 | Delamarche et al. | |
| 7,491,272 B2 | 2/2009 | Delamarche et al. | |
| 7,824,620 B2 | 11/2010 | Bau et al. | |
| 8,006,316 B2 | 8/2011 | Korchev et al. | |
| 8,277,756 B2 | 10/2012 | Gorka | |

(Continued)

OTHER PUBLICATIONS

R. Akeson, "Microsecond Timescale Discrimination Among Polycytidylic Acid, Polyadenylic Acid, and Polyuridylic Acid as Homopolymers or as Segments Within Single RNA Molecules," Biophys, J. vol. 77 3227-33 (Dec. 1999).

(Continued)

*Primary Examiner* — Hezron E Williams
*Assistant Examiner* — Truong Phan
(74) *Attorney, Agent, or Firm* — Cantor Colburn LLP; Vazken Alexanian

(57) ABSTRACT

A mechanism is provided for sensing molecules. A twin-nanopore probe includes a first channel and a second channel. A first pressure-controlled reservoir is connected to the first channel to generate a positive pressure. A second pressure-controlled reservoir is connected to the second channel to generate a negative pressure. A container includes ionic solvent with molecules, and a tip of the twin-nanopore probe is submerged in the container of the ionic fluid with the molecules. The first channel, the second channel, the first pressure-controlled reservoir, and the second pressure-controlled reservoir are filled with the ionic fluid. The first pressure-controlled reservoir drives the ionic fluid out of the first channel and the second pressure-controlled reservoir draws in the ionic fluid with the molecules and solvent through the second channel. A change in magnitude of ionic current through the second nanopore of twin-nanopore probe is detected when molecules pass through the second nanopore.

11 Claims, 10 Drawing Sheets

(56) References Cited

U.S. PATENT DOCUMENTS

| | | | |
|---|---|---|---|
| 8,323,585 | B2 | 12/2012 | Heavner |
| 8,597,594 | B2 | 12/2013 | Posner et al. |
| 8,821,796 | B2 * | 9/2014 | Peng .......................... 422/82.03 |
| 2002/0123154 | A1 | 9/2002 | Burshteyn et al. |
| 2008/0047330 | A1 | 2/2008 | Whitehouse et al. |
| 2010/0089757 | A1 * | 4/2010 | Ross et al. .................... 204/648 |
| 2010/0331194 | A1 | 12/2010 | Turner et al. |
| 2011/0112503 | A1 | 5/2011 | Ismagilov et al. |
| 2011/0279125 | A1 | 11/2011 | Bedell et al. |
| 2013/0183210 | A1 | 7/2013 | Wiyatno et al. |
| 2013/0337577 | A1 | 12/2013 | Pawlowski |

OTHER PUBLICATIONS

Heng J. B., et al., "Sizing DNA Using a Nanometer-diameter Pore," Biophys. J. vol. 87 2905-91 (Oct. 2004).

D. Juncker, et al., "Multipurpose Microfluidic Probe," Nature Materials, vol. 4, Aug. 2005, www.nature.com/naturematerials.

G. V. Kaigala, et al., "A Vertical Microfluidic Probe," Langmuir 2011, 27, 5686-5693, published Apr. 8, 2011.

Kasianowicz, et al., "Characterization of Individual Polynucleotide Molecules Using a Membrane Channel," Proc. Natl Acad. Sci. USA 93 13770-773 (1996).

Binquan Luan, et al., "Tribological Effects on DNA Translocation in a Nanochannel Coated with a Self-Assembled Monolayer," J. Phys. Cem. B., Dec. 3, 2010, 114, 17172-17176.

Meller A, et al., "Rapid Nanopore Discrimination Between Single Polynucleotide Molecules," Proc. Natl Acad. Sci. USA vol. 97, No. 3, 1079-84 (2000).

U.S. Appl. No. 13/439,265, filed Apr. 4, 2012; first named inventor: Ali Afzali-Ardakani.

* cited by examiner

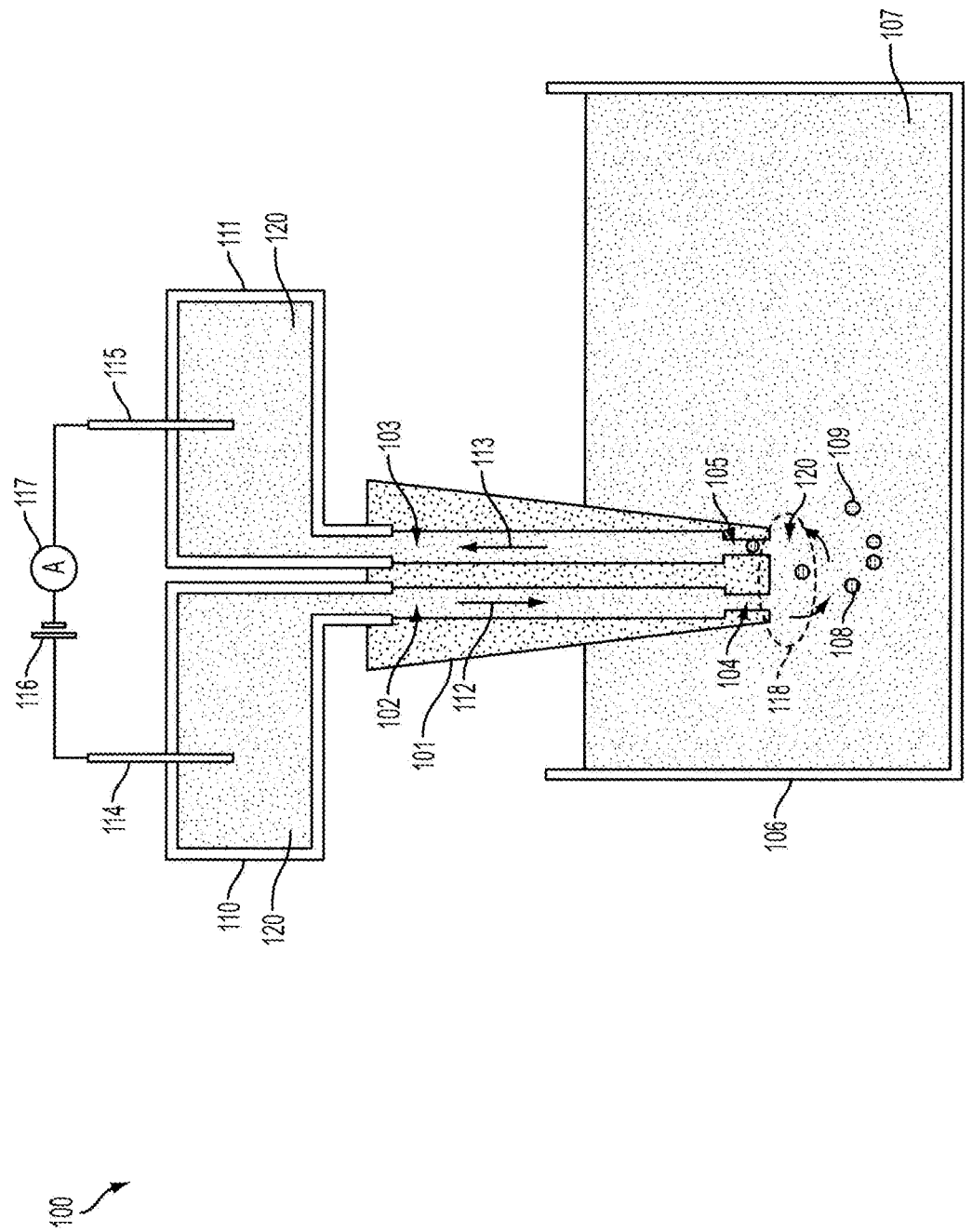

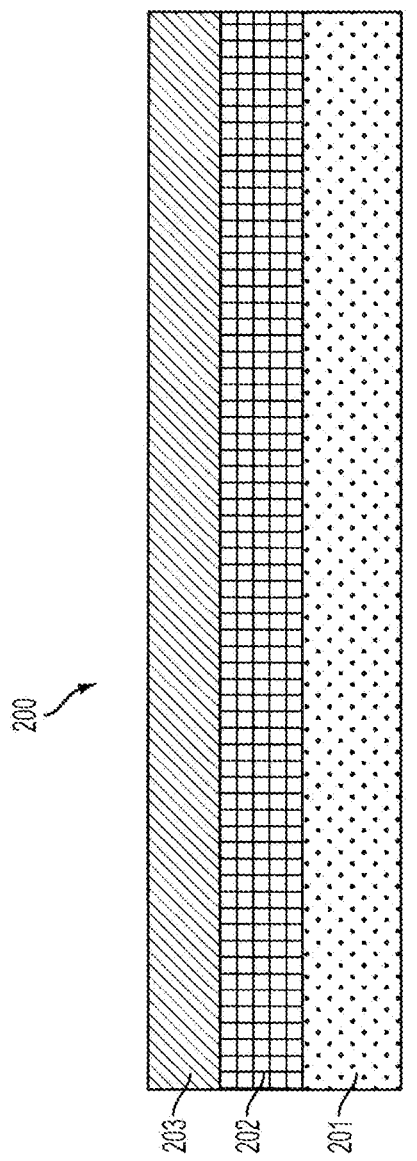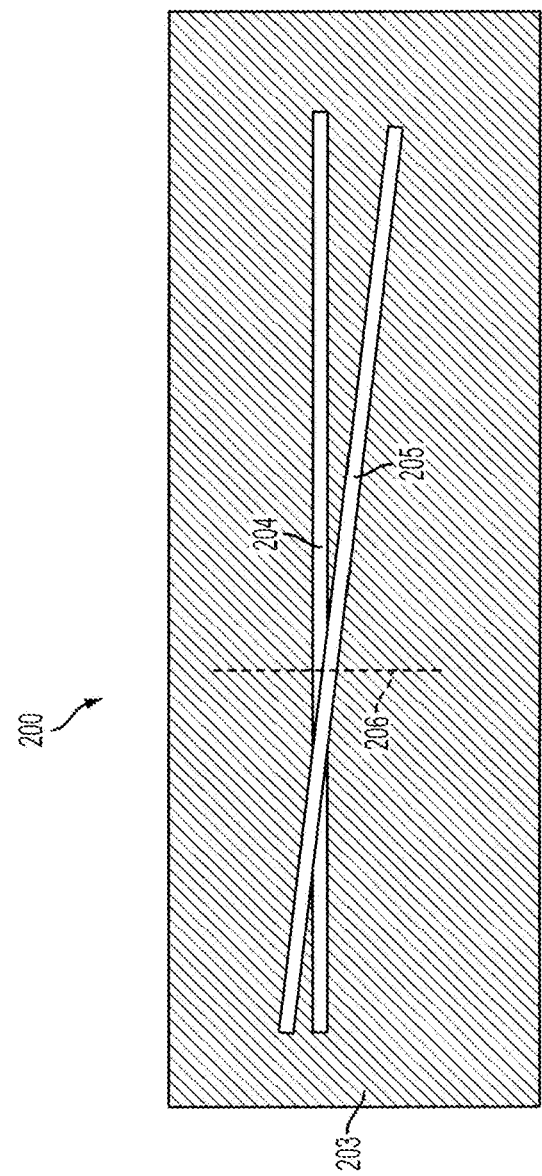

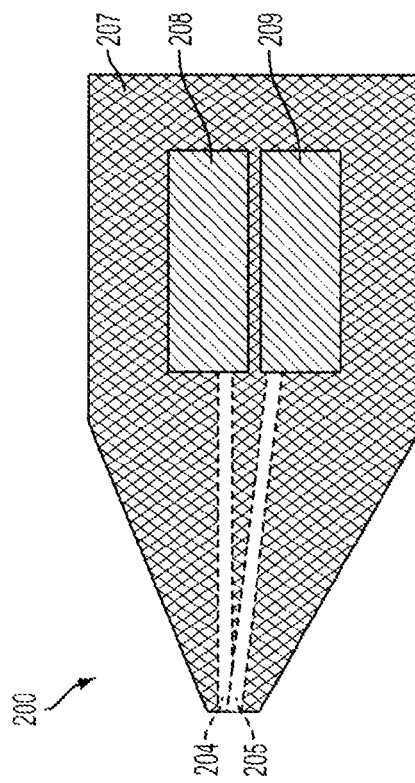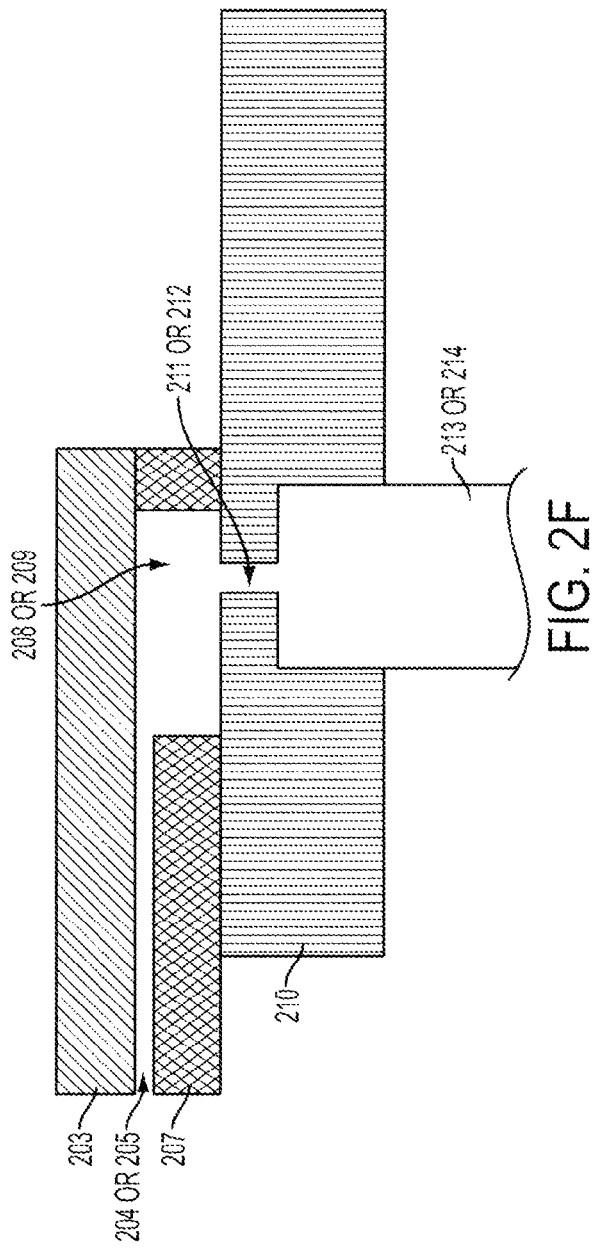

SENSING BIOMOLECULES USING SCANNING PROBE WITH TWIN-NANOPORE TO DETECT A CHANGE IN THE MAGNITUDE OF THE CURRENT THROUGH THE SECOND NANOPORE

BACKGROUND

The present invention relates to sensing molecules, and more specifically, to a scanning twin-nanopore probe for sensing molecules.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for sensing molecules is provided. A twin-nanopore probe has a first channel and a second channel. The first pressure-controlled reservoir is connected to the first channel, and the first pressure-controlled reservoir generates a positive pressure. A second pressure-controlled reservoir is connected to the second channel, and the second pressure-controlled reservoir generates a negative pressure. A container includes ionic fluid with molecules, and a tip of the twin-nanopore probe is submerged in the container of the ionic solvent with the molecules. The first channel, the second channel, the first pressure-controlled reservoir, and the second pressure-controlled reservoir are filled with the ionic fluid. The first pressure-controlled reservoir drives ionic fluid out of the first channel, and the second pressure-controlled reservoir draws in the ionic fluid with the molecules and solvent through the second channel. A change is detected in the magnitude of ionic current through the second nanopore of the twin-nanopore probe in response to at least one of the molecules passing through the second nanopore via the positive and negative pressure.

According to an embodiment, a method for sensing molecules is provided. A single-nanopore probe includes a channel, and a reservoir is connected to the channel. A container includes ionic fluid with molecules, and a tip of the single-nanopore probe is submerged in the container of the ionic fluid with the molecules. The channel and the reservoir are filled with the ionic fluid. A negative pressure inside the single-nanopore probe draws the molecules into channel. A flow of ionic current through the single-nanopore probe is measured to differentiate the molecules that flow into the channel.

According to an embodiment, a system for sensing molecules is provided. A twin-nanopore probe includes a first channel and a second channel. A first pressure-controlled reservoir is connected to the first channel, and the first pressure-controlled reservoir is configured to generate a positive pressure. A second pressure-controlled reservoir is connected to the second channel, and the second pressure-controlled reservoir is configured to generate a negative pressure. A container includes ionic solvent with molecules, and a tip of the twin-nanopore probe is submerged in the container of the ionic fluid with the molecules. The first channel, the second channel, the first pressure-controlled reservoir, and the second pressure-controlled reservoir are filled with the ionic fluid. The first pressure-controlled reservoir is configured to drive the ionic fluid out of the first channel, and the second pressure-controlled reservoir is configured to draw in the ionic fluid with the molecules and solvent through the second channel. The twin-nanopore probe is configured to facilitate a flow of ionic current that is measured to differentiate the molecules that flow through the second channel.

According to an embodiment, a system for sensing molecules is provided. A single-nanopore probe includes a channel, and a reservoir is connected to the channel. A container includes ionic fluid with molecules, and a tip of the single-nanopore probe is submerged in the container of the ionic fluid with the molecules. The channel and the reservoir are filled with the ionic fluid. A negative pressure inside the single-nanopore probe is configured to draw the molecules into channel. The single-nanopore probe is configured to facilitate a flow of ionic current that is measured to differentiate the molecules that flow into the second channel.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 1 is a cross-sectional view of a system having a twin-nanopore probe structure for sensing biomolecules according to an embodiment.

FIGS. 2A through 2F illustrate views of fabricating the twin-nanopore probe according to an embodiment, in which:

FIG. 2A illustrates a cross-sectional view of a structure in the process of being fabricated into the twin-nanopore probe;

FIG. 2B illustrates a top view of the structure with two nanotubes added;

FIG. 2C illustrates a cross-sectional view of the structure with an electrically insulating material of layer deposited;

FIG. 2D illustrates a top view of the structure after selective etching;

FIG. 2E illustrates a top view of the structure resulting in the twin-nanopore probe; and FIG. 2F illustrates a cross-sectional view of the twin-nanopore probe flipped and mounted on a holder.

DETAILED DESCRIPTION

Figure 2C:
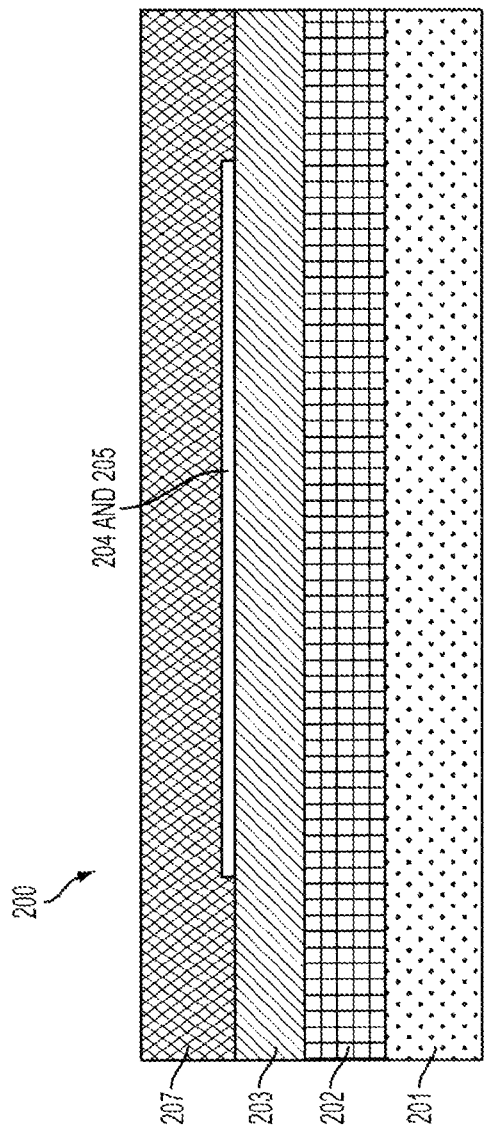

The present disclosure provides a mechanism to sense biomolecules using a twin-nanopore probe and ionic current measurements.

Highly negatively charged DNA molecules can be electrically driven through a pore of a few nanometers in diameter (nanopore). Nanopores have been proposed or demonstrated as sensors for rapid analysis of biomolecules (DNA, RNA, proteins, etc.) or their interactions. These conventional approaches require a relative large volume of samples (order of 10 µL (microliters)) and apply only on sensing charged molecules as the molecules are driven through the nanopore via electrical field.

An embodiment provides a twin-nanopore probe structure in which an active flow of ionic buffer is driven from one nanopore to another nanopore by pressure instead of electrical field. This allows the twin-nanopore probe to apply to both charged and non-charged molecules and the twin-nanopore probe can measure the local (10 nm (nanometers)) to microns away from the probe (i.e., localized area)). As this probe is actively scanning every area in the ionic buffer with molecules to be measured, the concentration of molecules is completely unlimited.

Now turning to the figures, FIG. 1 is a cross-sectional view of a system 100 having a schematic of the twin-nanopore probe structure for sensing biomolecules according to an embodiment.

The twin-nanopore probe 101 is a scanning probe made of electrically insulating material. The twin-nanopore probe 101 is made of two hollow channels 102 and 103. Both hollow channels 102 and 103 gradually taper into two nanopores 104 and 105 (respectively) at the sharp end of the twin-nanopore probe 101. The twin-nanopore probe 101 scans (e.g., back and forth, left to right, and/or up and down) in a container 106. The container 106 is filled with ionic solvent 107 (which may be ionic fluid) and with molecules 108 and 109 that need to be sensed.

Two pressure-controlled reservoirs 110 and 111 are filled with ionic buffer 120 and then connected (forming a seal) to the hollow channels 102 and 103 respectively. Each pressure-controlled reservoir 110 and 111 may be a syringe pump, mechanical pump, motorized pump, etc. The scanning twin-nanopore probe 101 is dipped into the solvent 107 (containing molecules 108 and 109) in the container 106 to sense the molecules 108 and 109 near the twin-nanopore probe 101, e.g., near the nanopore 104 and/or nanopore 105. The pressure-controlled reservoir 110 pressure-drives the ionic buffer 120 inside reservoir 110 into the hollow channel 102, and the ionic buffer 120 flows from the reservoir 110 into the container 106 and locally mixes with the solvent 107. Concurrently, the mixed ionic buffer 120 (together with molecules 108 and 109) in the container 106 is pressure driven into hollow channel 103 through the nanopore 105 and flows into the pressure-controlled reservoir 111 by applying a negative pressure in reservoir 111. The flow directions (caused by the positive pressure of the reservoir 110 and the negative pressure of the reservoir 111) of the ionic buffer 120 are indicated by arrows 112 and 113. Depending on the ratio of the flow rate of pressures 112 and 113, a flow profile will form in a region of the container 106, defined as area 118 (i.e., region within the container 106). Molecules 108 and 109 inside the area 118 are pulled (one at a time) into the nanopore 105 for sensing by the combination of the positive pressure 112 and the negative pressure 113.

In one case, the ionic buffer 120 in the pressure-controlled reservoirs 110 and 111 may be different than the solvent 107 in the container 106. For example, when the solvent 107 is a non-conductive solvent and when the ionic buffer 120 in pressure-controlled reservoirs 110 and 111 is conductive, the whole system can still work for detecting molecules 108 and 109 using ionic current through nanopore 105. In another case, the ionic buffer 120 in the pressure-controlled reservoirs 110 and 111 may be the same as the solvent 107 (but the solvent 107 includes the molecules 108/109) in the container 106. For example, both the solvent 107 and the ionic buffer 120 are conductive.

Electrochemical electrodes 114 and 115, such as Ag/AgCl wires, are dipped into the reservoirs 110 and 111 respectively. Voltage of voltage source 116 is applied between the two electrodes 114 and 115 and the resulting ionic current is measured by ammeter 117.

Figure 8:
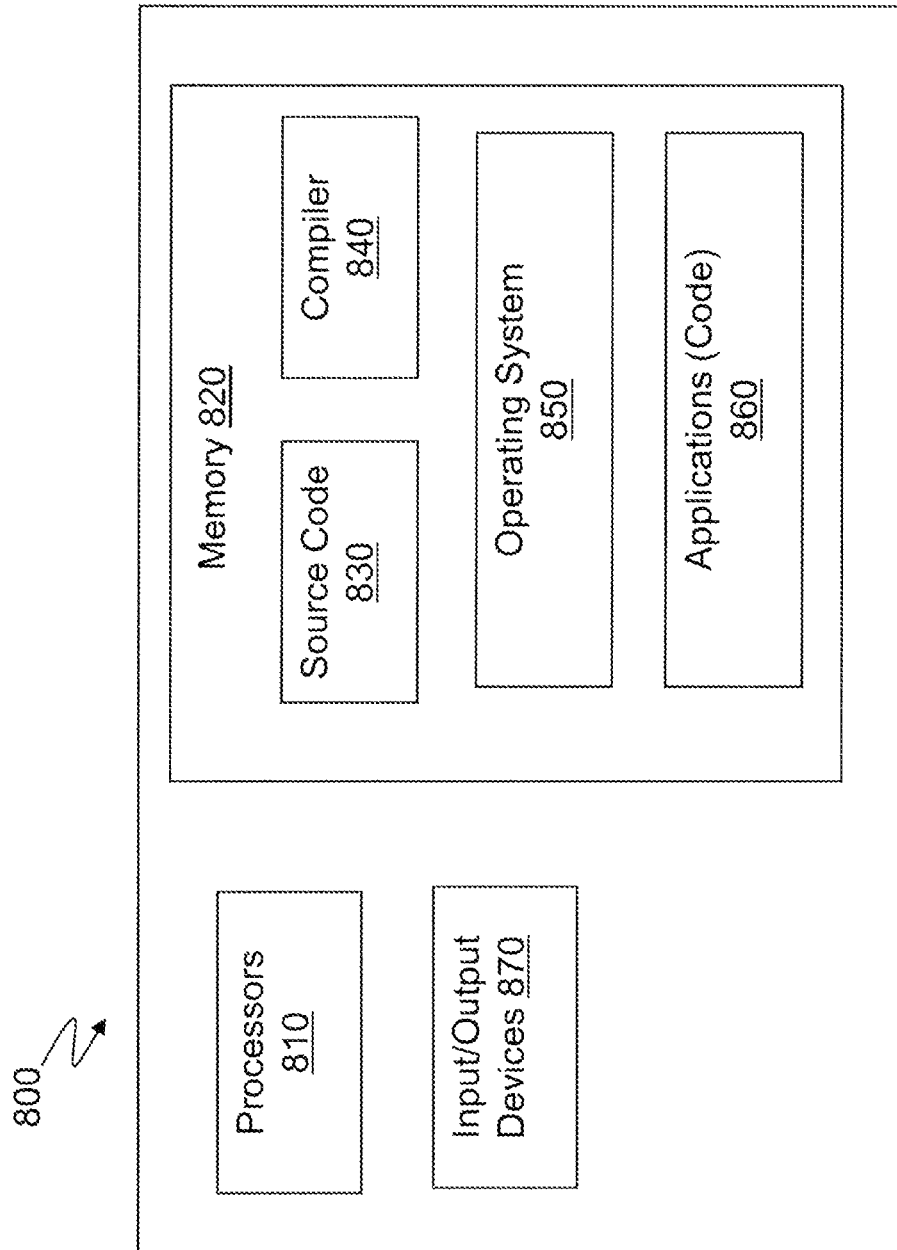
FIG. 8 is a block diagram that illustrates an example of a computer (computer setup) having capabilities, which may be included in and/or combined with embodiments.

While molecules 108 and 109 pass through nanopore 105, a change in the ionic current (measured via ammeter 117 which may be connected to/implemented in a computer 800 in FIG. 8) is detected. The amount of change in the measured ionic current depends on the size and surface charge of the molecule 108/109. In this way, each molecule 108/109 is sensed as it passes through nanopore 105.

When no molecule 108 or 109 is in the nanopore 105 and voltage of the voltage source 116 is applied, a baseline ionic current (baseline waveform) flows from the electrode 114, through the reservoir 110 (i.e., via ionic buffer 120), through the hollow channel 102 (i.e., via ionic buffer 120), through nanopore 104 (i.e., via ionic buffer 120), out into the mixed ionic buffer 120 (which has mixed with the solvent 107) in the container 106 (only within a small distance around the tip of the twin-nanopore probe 101), back into the nanopore 105, through the hollow channel 103, into the reservoir 111, and into the electrode 115. The baseline ionic current is the measurement (via ammeter 117) when no molecule 108 and 109 is in the nanopore 105.

However, when a molecule 108 or 109 is in the nanopore 105 and the voltage of the voltage source 116 is applied, the ionic current (modulated waveform) flows from the electrode 114, through the reservoir 110 (i.e., via ionic buffer 120), through the hollow channel 102, through nanopore 104, out into the mixed ionic buffer 120 in the container 106 (only within a small distance around the tip of the twin-nanopore probe 101), back into the nanopore 105 (in which the ionic current is affected/changed by the particular molecule 108 or 109), through the hollow channel 103, into the reservoir 111, and into the electrode 115 (to be measured by the ammeter 117).

As understood by one skilled in the art, the ionic buffer 120 conducts electricity (e.g., via ions) to produce the ionic current that is measured by the ammeter 117. FIG. 8 illustrates an example of a computer 800 which may implement, control, and/or regulate the voltage of the voltage source 116, measurements of the ammeter 117, and respective pressures 112 and 113 of the pressure-controlled reservoirs 110 and 111. Also, the baseline waveform of the baseline ionic current and the modulated/changed waveform of the ionic current (affected by the molecule 108 or 109 inside the nanopore 105) can be displayed and recorded by the computer 800. For example, a molecule 108 or 109 within the nanopore 105 may change/affect the magnitude and/or time duration of the measured ionic current, and this waveform (e.g., current on the y-axis and time on the x-axis) is displayed on the display of the computer 800 for each measurement of the ionic current.

Note that ionic buffer 120 and solvent 107 could be the same or totally different. In the case that 107 is non-conductive solvent, conductive ionic buffer 120 will still facilitate the flow of the ionic current (measured by ammeter 117) so that molecules 108 or 109 can still be sensed.

Regarding the details of ionic current (measured by ammeter 117), when voltage of voltage source 116 is applied between two electrodes 114 and 115 (for example, positive terminal of the voltage is on electrode 114 while the negative terminal of the voltage is on electrode 115) positive ions are driven from electrode 114 to the channel 102, then driven out of nanopore 104 into the area 118, then driven into nanopore 105 and into channel 103, and then driven to reservoir 111 and onto electrode 115 where the positive ions react with electrodes 115. Negative ions do the reverse. This illustrates an example of how the measured ionic current (measured by ammeter 117) forms.

In the system 100, each part of the ionic buffer/solution 120 in reservoir 110, channel 102, nanopore 104, area 118 (mixed in the container 106), nanopore 105, channel 103, and reservoir 111 acts like electrical resistance in series. The resistances of the ionic buffer 120 inside the nanopore 104 and 105 are orders of magnitude larger than the other parts (reservoir 110, channel 102, area 118, channel 103, and reservoir 111) as the nanopores 104 and 105 have the smallest cross-section (orders of magnitude smaller). As such, the ionic current is mainly dependent on the sum of the resistance of the ionic buffer 120 in nanopores 104 and 105. Consequently, only molecules 108 or 109 inside the nanopore 104 or 105 can induce a large change of the baseline ionic current (measured by ammeter 117). If one makes the size of the nanopore 105 small enough so that only one molecule 108 or 109 can get in (i.e., fit) at any given time (as discussed herein), the ionic current (measured by ammeter 117) has single molecule resolution.

FIGS. 2A through 2F (generally referred to as FIG. 2) illustrate views of fabricating the twin-nanopore probe 101 (and also a single-nanopore probe 301 shown in FIG. 3) according to an embodiment.

FIG. 2A is a cross-sectional view of a structure 200 that is in the process of being fabricated into the twin-nanopore probe 101. As shown in FIG. 2A, layer 201 is the substrate, such as a Si wafer. Layer 202 is a sacrificial material that can be easily etched later on, such as $SiO_2$. Layer 203 is an electrically insulating material, such as $Si_3N_4$. The insulating material of layer 203 is the housing for the twin-nanopore probe 101.

FIG. 2B is the top view of the structure 200. Two nanotubes 204 and 205 are inserted/placed in the insulating material of layer 203. The two nanotubes 204 and 205 may be carbon nanotubes, glass nanotubes, etc. The two nanotubes 204 and 205 overlaps each other (for example, 205 covers on top of 204). Later in the fabrication process, an etching step can be done to cut the two nanotubes 204 and 205 at a location illustrated as 206 (shown with dashed lines). Depending on where the location 206 is chosen, the distance between the ends of the two nanotubes 204 and 205 at the cutting ends will vary. Note that when forming the single-nanopore probe 301, only one nanotube 204 (or 205) is inserted; otherwise, the fabrication process remains the same except one nanotube 204 is being utilized.

Figure 2D:
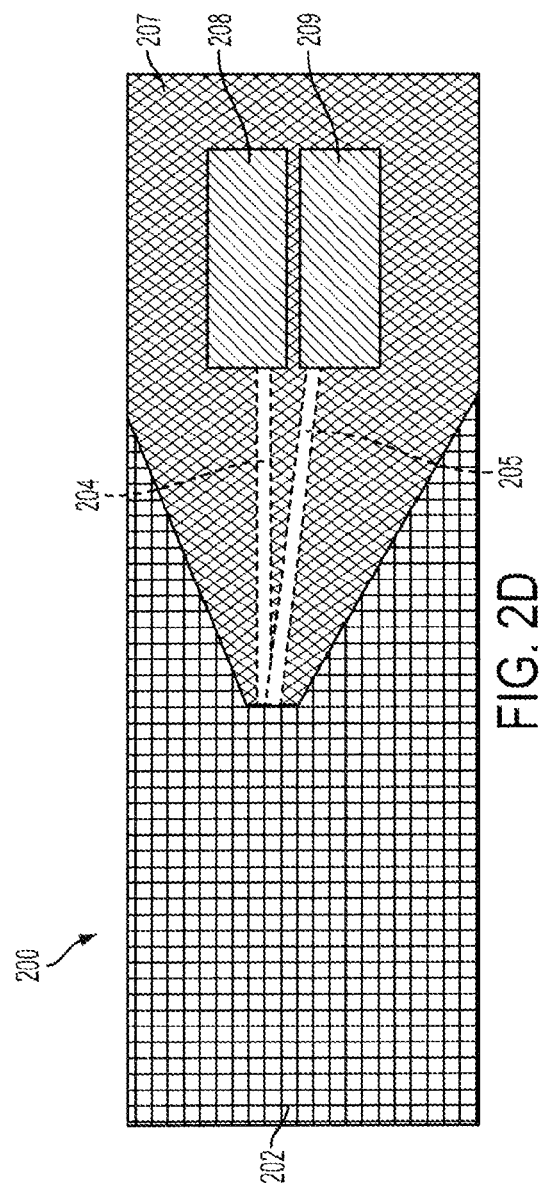

FIG. 2C is a cross-sectional view of the structure 200. Before etching, an electrically insulating material of layer 207, such as $Si_3N_4$, is deposited on top of the nanotubes 204 and 205 to seal the nanotubes 204 and 205, as shown in FIG. 2C. Material of layer 207, nanotubes 204 and 205 (at the location 206), and material of layer 203 are selectively etched via photolithography and reactive ion etching to provide the result shown in FIG. 2D. FIG. 2D shows the resulting structure 200 in the top view after utilizing a mask (not shown) to etch away material. In the structure 200, most of the area is etched down to the layer 202 in the desired shape according to the mask, while rectangular areas 208 and 209 are only etched down to layer 203 (via another mask not shown).

Then, all the material of layer 202 is etched away using a wet etchant, such as HF (hydrogen fluoride), and the completed twin-nanopore probe 101 can be lifted off from the substrate layer 201, as shown in the top view of the structure 200 in FIG. 2E. The remaining parts of nanotubes 204 and 205 are corresponding to nanopores 104 and 105 respectively shown in FIG. 1.

As shown in FIG. 2F (cross-sectional view), the twin-nanopore probe 101 is flipped and mounted on a holder 210, which can be made of any electrically-insulating materials. An o-ring, glue, or epoxy can also be employed to enhance the sealing between the twin-nanopore probe 101 and the holder 210. Holes 211 and 212 can be made through the holder 210. One end of the hole 211 (or 212) is aligned to window area 208 (or 209), while the other end of the hole 211 (or 212) is adapted to a fluidic tube 213 (or 214) to connect to the reservoirs 110 (or 111). The window area 208 (or 209), the hole 211 (or 212), and the fluidic tube 213 (or 214) respectively correspond to the channel 102 (or 103) in FIG. 1.

Figure 3:
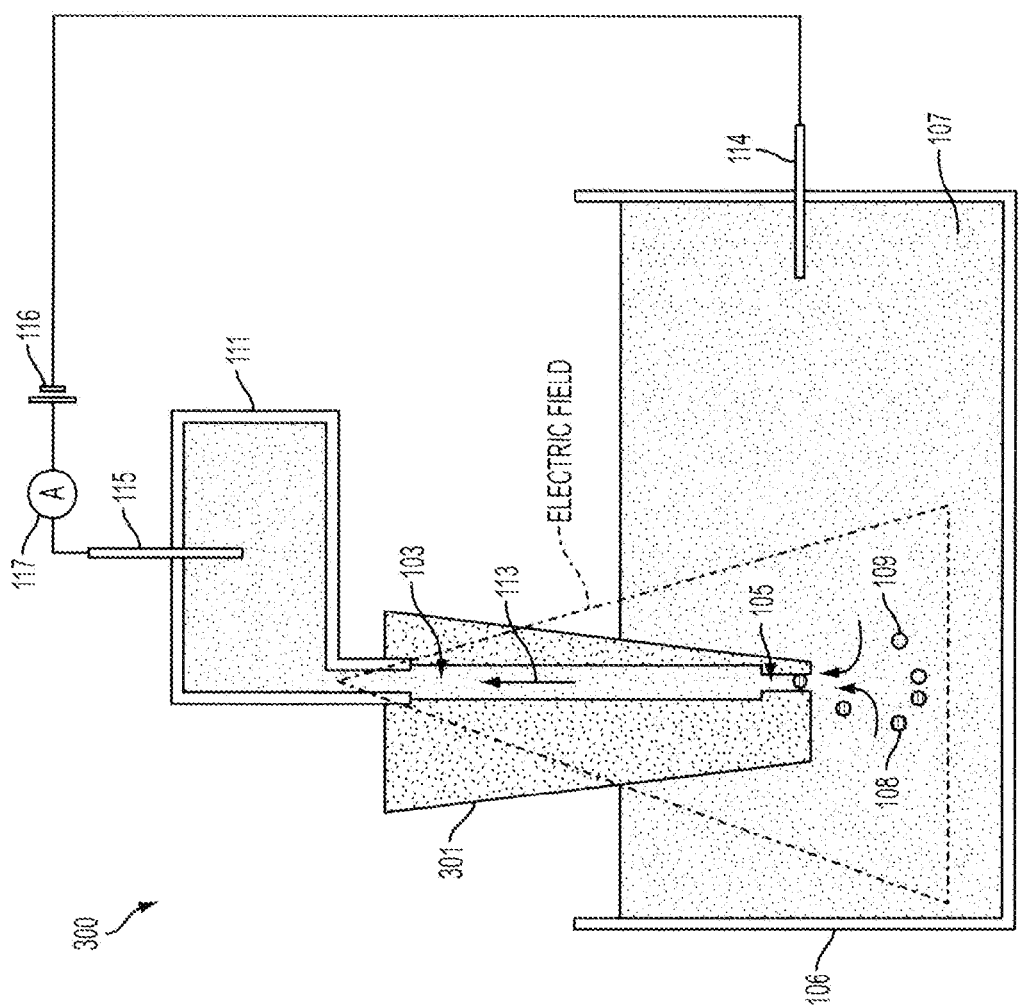
FIG. 3 is a cross-sectional view of a system having a single-nanopore probe structure for sensing biomolecules according to an embodiment.

FIG. 3 is a cross-sectional view of a system 300 having a schematic of a single-nanopore probe 301 structure for sensing biomolecules according to an embodiment. As can be seen, features of the single-nanopore probe 301 structure correspond to features of the twin-nanopore probe 101 structure discussed herein.

If solvent 107 (with molecules 108 and 109 to be sensed) is electrically conductive, a single-nanopore probe 301 can also be employed. The single-nanopore probe 301 can be realized by using only one nanopore from the twin-nanopore probe 101 or specially making a single nanopore probe. In this case, the solvent 107 and the ionic buffer 120 are the same.

The single-nanopore probe 301 is a scanning probe made of electrically insulating material. The single-nanopore probe 301 is made of one hollow channel 103. The hollow channel 103 gradually tapers into nanopores 105 at the sharp end of the single-nanopore probe 301. The single-nanopore probe 301 scans (e.g., back and forth or left to right) in the container 106. The container 106 is filled with solvent 107 (which is the same as the ionic buffer 120) and with molecules 108 and 109 that need to be sensed as discussed herein.

The pressure-controlled reservoir 111 is filled with the solvent 107 (which is the same as the ionic buffer 120) and connected to the hollow channel 103. As noted above, the pressure-controlled reservoir 111 may be a syringe pump, mechanical pump, motorized pump, etc. The scanning single-nanopore probe 301 is dipped into the container 106 to sense the molecules 108 and 109 which enter the nanopore 105 near the opening of the single-nanopore probe 301.

In one example, the pressure-controlled reservoir 111 may apply a negative pressure (relative to the atmosphere pressure) and/or may have a negative pressure applied to the pressure-controlled reservoir 111 to draw (vacuum) the solvent 107 (i.e. ionic buffer) into the nanopore 105. By having the pressure-controlled reservoir apply negative pressure, the single-nanopore probe 301 is configured to draw in both non-charged and electrically charged particles/molecules 108 and 109, along with the solvent 107.

Continuing the example, the solvent 107 (i.e. ionic buffer) in the container 106 is pressure driven into hollow channel 103 and flows into the pressure-controlled reservoir 111 by applying the negative pressure in pressure-controlled reservoir 111. The flow direction (caused by the negative pressure of the reservoir 111) of the solvent 107 (i.e., ionic buffer) is indicated by arrow 113. Molecules 108 and 109 inside the container 106 are pulled into the nanopore 105 for sensing.

Electrochemical electrodes 114 and 115, such as Ag/AgCl wires, are dipped into the container 106 and reservoir 111, respectively. Voltage of voltage source 116 is applied between the two electrodes 114 and 115 and the resulting ionic current is measured by ammeter 117.

While molecules 108 and 109 pass through the nanopore 105, a change in the ionic current (measured via ammeter 117) is detected/measured. The amount of change in the measured ionic current depends on the size and surface charge of the molecule 108 or 109. In this way, each molecule 108 or 109 is sensed as it passes through nanopore 105 as discussed herein.

In a case when the particles/molecules 108 and 109 to be measured are electrically charged (as understood by one skilled in the art), the reservoir 111 does not need to be pressure driven as an electrical field created by voltage of the voltage source 116 drives the charged molecules 108 and 109 into the nanopore 105. Pressure may (only) be needed for non-charged particles/molecules.

In one case, both negative pressure and the electric field generated by voltage of the voltage source 116 may be utilized to capture/draw in electrically charged molecules 108 and 109 (both charged and non-charged) into the nanopore 105 for sensing.

Figure 4:
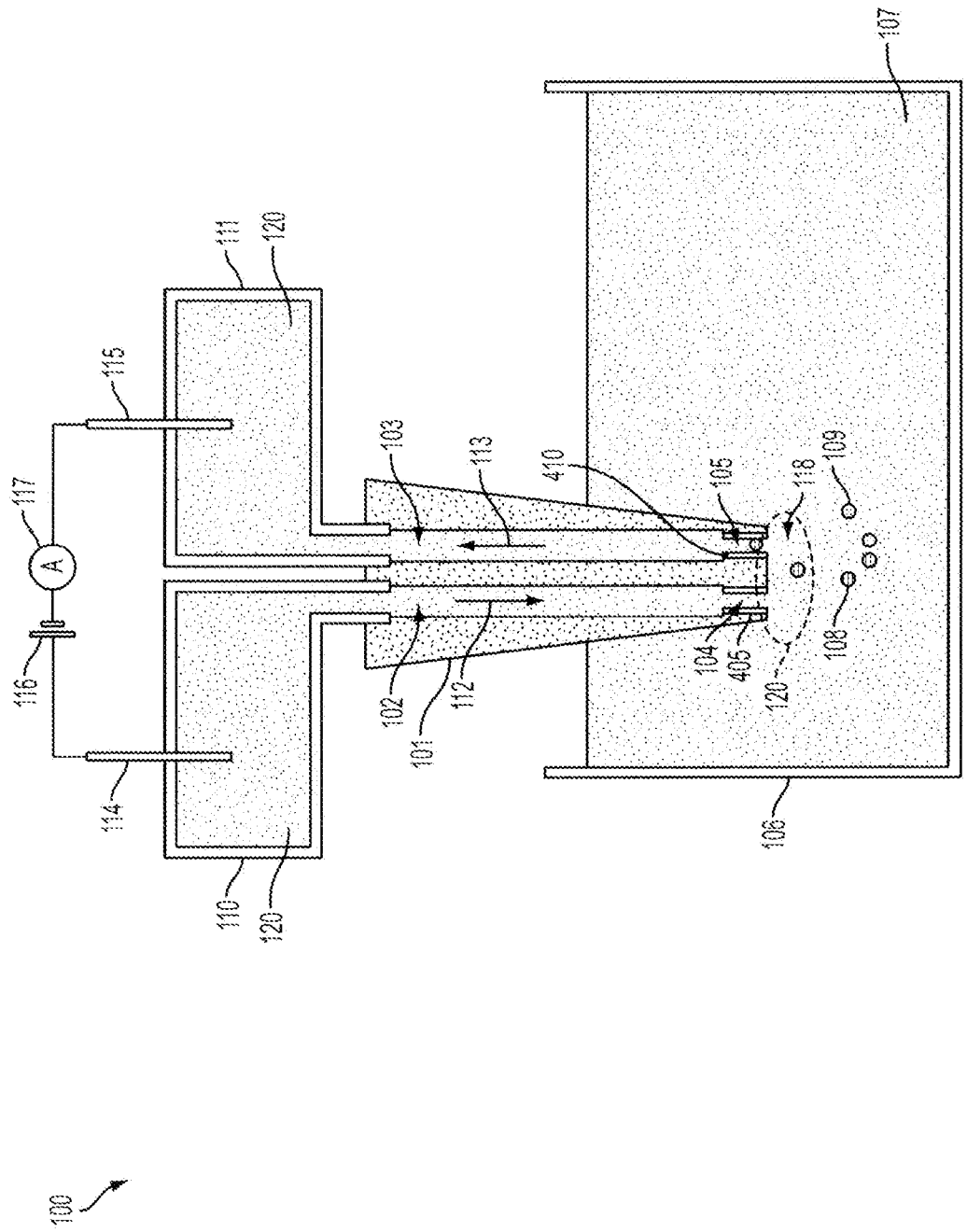
FIG. 4 is a cross-sectional view of the system having the twin-nanopore probe structure in which the nanopores are coated with an organic layer according to an embodiment.

FIG. 4 is a cross-sectional view of the system 100 having the twin-nanopore probe 101 for sensing biomolecules according to an embodiment. FIG. 4 is identical to FIG. 1 except the nanopores 104 and 105 are now respectively coated with organic layers 405 and 410. The organic layers 405 and 410 may be the same in one case, and may be different in another case. The organic layers 405 and 410 may have a different interaction with different types of molecules 108 and 109. For example, the organic layer 405 and 410 may interact with a particular molecule 108 (and/or 109) by sticking to the molecule 108, which causes a longer time duration of that particular molecule 108 inside the nanopore 105. As the ionic current (measured by the ammeter 117 when the molecule 108 is inside the nanopore 105) is monitored in real time and from the time trace of ionic current (graph/plot), the difference in time duration of molecules inside nanopore 105 can be resolved and employed to differentiate molecules.

For example, if molecules 108 or 109 are proteins of viruses or antigens, then organic coating 405 or 410 can be antibodies. If molecules 108 or 109 are single strand DNA molecules, organic coating 405 or 410 can be complementary DNA bases or DNA oligomers.

Figure 5:
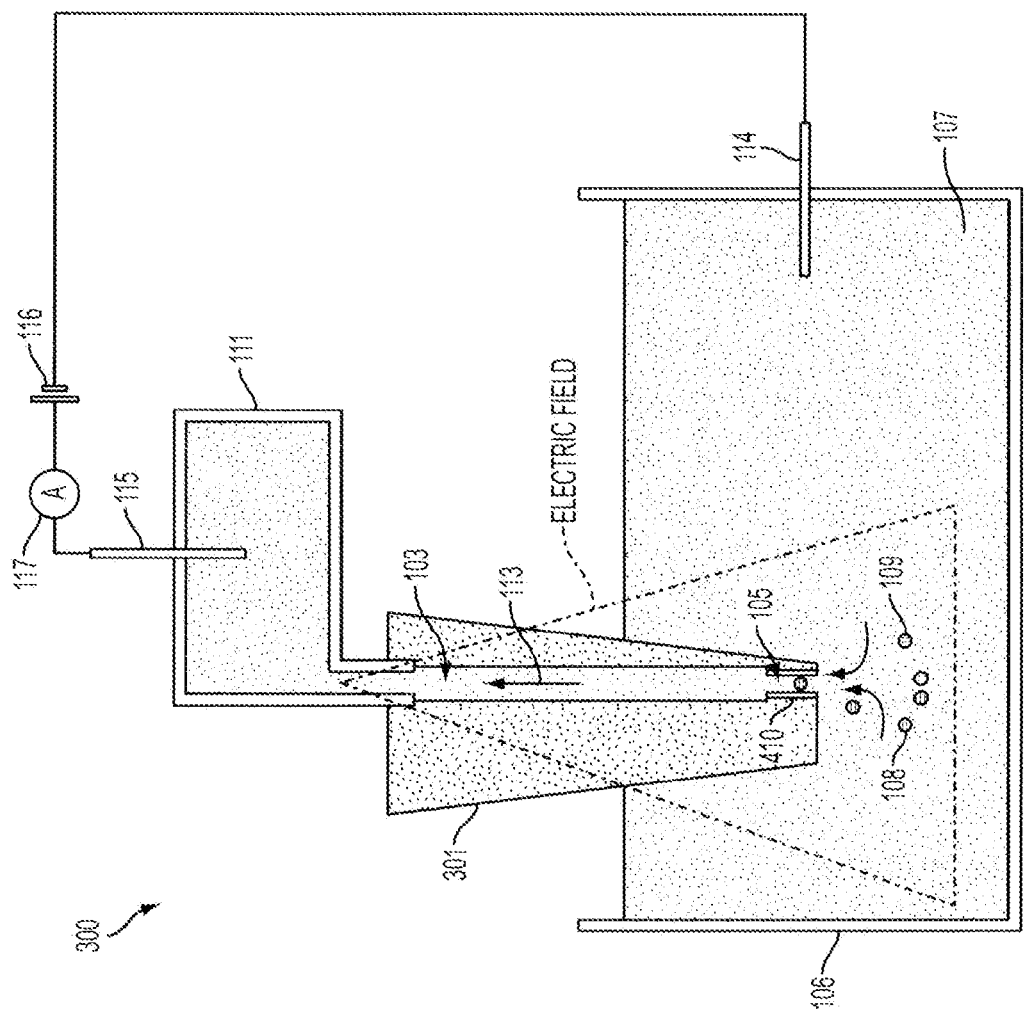
FIG. 5 is a cross-sectional view of a system having the single-nanopore probe structure in which the nanopore is coated with an organic layer according to an embodiment.

FIG. 5 is a cross-sectional view of the system 300 having the single-nanopore probe 301 structure for sensing biomolecules according to an embodiment. FIG. 5 is identical to FIG. 3 except the nanopore 105 is now coated with organic layer 410. The organic layer 410 is configured to interact with the molecules 108 and 109 as discussed above for FIG. 4.

Figure 6:
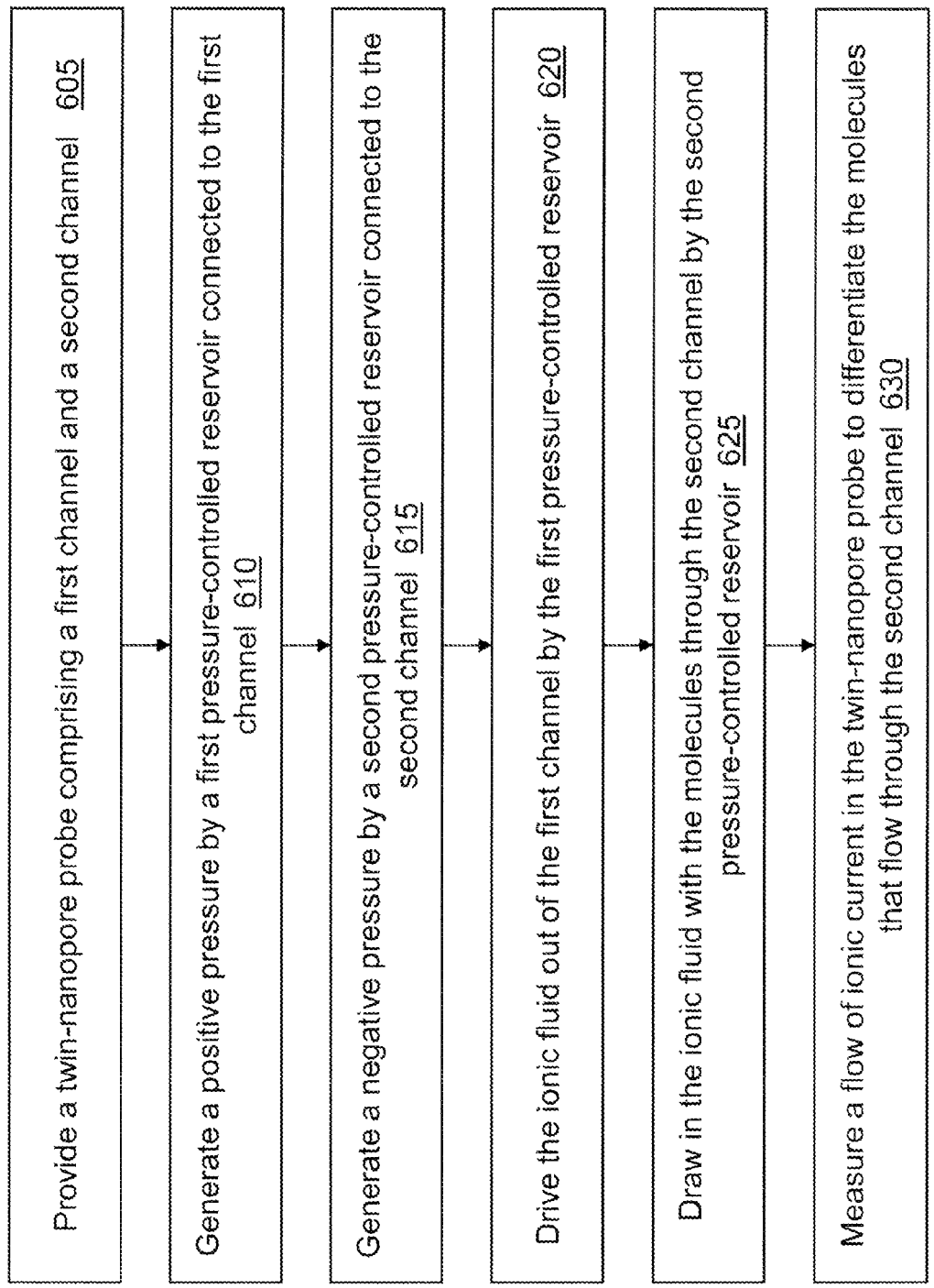
FIG. 6 is a flow diagram illustrating a method of sensing molecules via a twin-nanopore probe structure according to an embodiment.

FIG. 6 is a method 600 for sensing molecules via the twin-nanopore probe 101 according to an embodiment. Reference can be made to FIGS. 1, 2, and 4.

A twin-nanopore probe 101 with a first (hollow) channel 102 and a second (hollow) channel 103 is provided at block 605. A first pressure-controlled reservoir 110 is connected to the first channel 102 to generate a positive pressure 112 at block 610.

A second pressure-controlled reservoir 111 is connected to the second channel 103 to generate a negative pressure 113 at block 615. A container 106 includes solvent 107 (fluid) with molecules 108 and 109, and a tip of the twin-nanopore probe 101 is submerged in the container 106 of the solvent 107 with the molecules 108 and 109. The first channel 102, the second channel 103, the first pressure-controlled reservoir 110, and the second pressure-controlled reservoir 111 are filled with the ionic buffer 120.

The first pressure-controlled reservoir 110 drives the ionic buffer 120 out of the first channel 102 by the positive pressure 112 at block 620. The second pressure-controlled reservoir 111 draws in the molecules 108 and 109 with the mixed ionic buffer 120 (with solvent 107 and molecules 108 and 109) through the second channel 103 by the negative pressure 113 at block 625.

The flow of ionic current in the twin-nanopore probe 101 is measured (via the ammeter 117) to differentiate the molecules 108 and 109 that flow through the second channel 103 at block 630. For example, each molecule 108 and 109 is individually measured within the nanopore 105 (by measuring the ionic current via the ammeter 117, e.g., detecting the change in ionic current from a baseline value (waveform) when no molecule 108/109 is in the nanopore 105 to the modified ionic current (waveform) when the particular molecule 108/109 is inside the nanopore 105). Voltage of the voltage source 116 is applied to generate the ionic current via electrodes 114 and 115.

Further, the method includes defining a region (e.g., the area 118) according to the positive pressure 112 generated by the first pressure-controlled reservoir 110 and the negative pressure 113 generated by the second pressure-controlled reservoir 111. Accordingly, the region (area 118) comprises the molecules 108 and 109 to be drawn into the second channel 103 via the nanopore 105.

The method in which the first channel 102 comprises an elongated section (e.g., the tubular section between the reservoir 110 and the nanopore 104) connected to a first nanopore 104, and the first nanopore 104 is an exit for the positive pressure 112 generated by the first pressure-controlled reservoir 110. The method in which the second channel 103 comprises an elongated section (e.g., the tubular section between the reservoir 111 and the nanopore 105) connected to a second nanopore 105, and the second nanopore 105 is an entrance (inlet) for the negative pressure 113 generated by the second pressure-controlled reservoir 111.

The method in which inner surfaces of the second nanopore 105 are coated with an organic layer 410, and the organic layer 410 interacts differently with the different types of molecules 108 and 109.

The method in which a first electrode 114 is in the first pressure-controlled reservoir 110 and a second electrode 115 is in the second pressure-controlled reservoir 111, and a voltage source 116 is connected to the first electrode 114 and the second electrode 115. The voltage source 116 generates the ionic current to measure (via the ammeter 117) each of the molecules 108 and 109 that flow through the second channel 103 (e.g., while in the nanopore 105).

Figure 7:
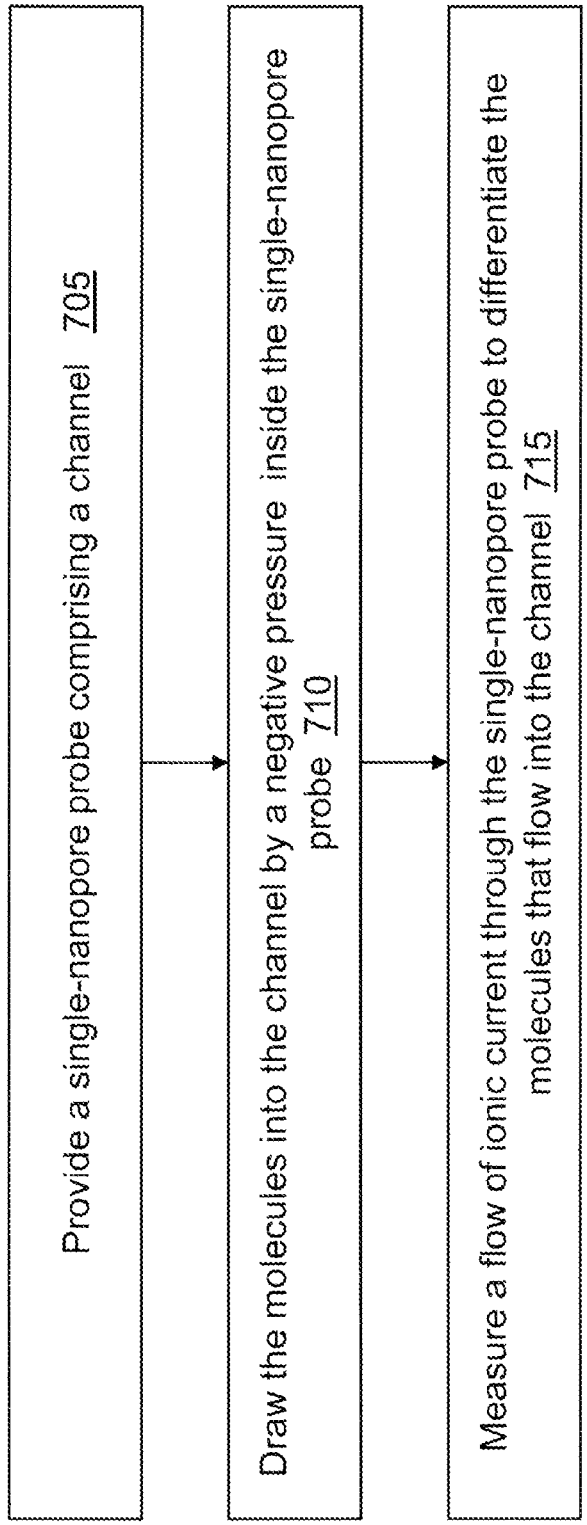
FIG. 7 is a flow diagram illustrating a method of sensing molecules via a single-nanopore probe structure according to an embodiment.

FIG. 7 is a method 700 for sensing molecules via the singe-nanopore probe 301 structure according to an embodiment. Reference can be made to FIGS. 2 and 3. In this case, the solvent 107 is electrically conducting and is the same as the ionic buffer 120.

The single-nanopore probe 301 structure includes a channel 103 at block 705. A pressure-controlled reservoir 111 is connected to the channel 103. A container 106 comprises solvent 107 (i.e., ionic buffer) with molecules 108 and 109, and the tip of the single-nanopore probe 301 is submerged in the container 106 of the solvent 107 (ionic buffer) with the molecules 108 and 109. The channel 103 and the pressure-controlled reservoir 111 are filled with the same solvent 107 (ionic buffer) (e.g., but without the molecules 108 and 109).

The molecules 108 and 109 are drawn (pulled) into the channel 103 by the negative pressure 113 inside the single-nanopore probe 301 (and the container 106) at block 710. A flow of ionic current through the single-nanopore probe 301 is measured (via the ammeter 117) to differentiate the molecules 108 and 109 that flow into the channel 103 at block 715.

The method in which one electrode 115 is in the pressure-controlled reservoir and another electrode 114 is in the container 106, and a voltage source 116 is connected to one electrode 115 and the other electrode 114. The method in which the voltage source 116 generates/causes the ionic current to differentiate the molecules 108 and 109 (while in the nanopore 105) that flow into the channel 103.

FIG. 8 illustrates an example of a computer 800 (e.g., as part of the computer setup for testing and analysis) having capabilities, which may be included in exemplary embodiments. Various methods, procedures, modules, flow diagrams, tools, applications, circuits, elements, and techniques discussed herein may also incorporate and/or utilize the capabilities of the computer 800. Moreover, capabilities of the computer 800 may be utilized to implement features of exemplary embodiments discussed herein. One or more of the capabilities of the computer 800 may be utilized to implement, to connect to, and/or to support any element discussed herein (as understood by one skilled in the art) in FIGS. 1-7. For example, the computer 800 which may be any type of computing device and/or test equipment (including ammeters, voltage sources, connectors, etc.). Input/output device 870 (having proper software and hardware) of computer 800 may include and/or be coupled to the nanodevices and structures discussed herein via cables, plugs, wires, electrodes, etc. Also, the communication interface of the input/output devices 870 comprises hardware and software for communicating with, operatively connecting to, reading, and/or controlling voltage sources, ammeters, and ionic current traces (e.g., magnitude and time duration of ionic current), etc., as discussed herein. The user interfaces of the input/output device 870 may include, e.g., a track ball, mouse, pointing device, keyboard, touch screen, etc., for interacting with the computer 800, such as inputting information, making selections, independently controlling different voltages sources, and/or displaying, viewing and recording ionic current traces for each base, molecule, biomolecules, etc.

Generally, in terms of hardware architecture, the computer 800 may include one or more processors 810, computer readable storage memory 820, and one or more input and/or output (I/O) devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a data signal processor (DSP), or an auxiliary processor among several processors associated with the computer 800, and the processor 810 may be a semiconductor based microprocessor (in the form of a microchip) or a macroprocessor.

The computer readable memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the computer readable memory 820 may include one or more separate programs, each of which comprises an ordered listing of executable instructions for implementing logical functions. The software in the memory 820 includes a suitable operating system (O/S) 850, compiler 840, source code 830, and one or more applications 860 of the exemplary embodiments. As illustrated, the application 860 comprises numerous functional components for implementing the features, processes, methods, functions, and operations of the exemplary embodiments.

The operating system 850 may control the execution of other computer programs, and provides scheduling, input-output control, file and data management, memory management, and communication control and related services.

The application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as (a) an object oriented programming language, which has classes of data and methods, or (b) a procedure programming language, which has routines, subroutines, and/or functions.

The I/O devices 870 may include input devices (or peripherals) such as, for example but not limited to, a mouse, keyboard, scanner, microphone, camera, etc. Furthermore, the I/O devices 870 may also include output devices (or peripherals), for example but not limited to, a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or an intranet. The I/O devices 870 may be connected to and/or communicate with the processor 810 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 860 is implemented in hardware, the application 860 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for sensing molecules, the method comprising:
   providing a twin-nanopore probe comprising a first channel and a second channel;
   generating a positive pressure by a first pressure-controlled reservoir connected to the first channel;
   generating a negative pressure by a second pressure-controlled reservoir connected to the second channel;
   wherein a container comprises solvent with the molecules, a tip of the twin-nanopore probe being submerged in the container of the solvent with the molecules; and
   wherein the first channel, the second channel, the first pressure-controlled reservoir, and the second pressure-controlled reservoir are filled with an ionic fluid;
   driving the ionic fluid out of the first channel by the first pressure-controlled reservoir;
   drawing in the ionic fluid, mixed with the molecules and the solvent, through the second channel by the second pressure-controlled reservoir; and
   detecting a change in a magnitude of ionic current through the second nanopore of the twin-nanopore probe in response to at least one of the molecules passing through the second nanopore via the positive and negative pressures.

2. The method of claim 1, further comprising defining a region according to the positive pressure generated by the first pressure-controlled reservoir and the negative pressure generated by the second pressure-controlled reservoir.

3. The method of claim 2, wherein the region comprises the molecules to be drawn into the second channel.

4. The method of claim 1, wherein the first channel comprises an elongated section connected to a first nanopore.

5. The method of claim 4, wherein the first nanopore is an exit for the positive pressure generated by the first pressure-controlled reservoir.

6. The method of claim 5, wherein the second channel comprises an elongated section connected to a second nanopore.

7. The method of claim 6, wherein the second nanopore is an entrance for the negative pressure generated by the second pressure-controlled reservoir.

8. The method of claim 7, wherein inner surfaces of the second nanopore are coated with an organic layer; and
   wherein the organic layer interacts differently with the molecules.

9. The method of claim 1, wherein a first electrode is in the first pressure-controlled reservoir and a second electrode is in the second pressure-controlled reservoir.

10. The method of claim 9, wherein a voltage source is connected to the first electrode and the second electrode.

11. The method of claim 10, wherein the voltage source generates the ionic current to measure each of the molecules that flow through the second nanopore.

* * * * *